US005993781A

United States Patent [19]
Snell et al.

[11] Patent Number: 5,993,781
[45] Date of Patent: Nov. 30, 1999

[54] FLUTICASONE PROPIONATE NEBULIZABLE FORMULATIONS

[75] Inventors: Dorothy Jill Snell; Li Fong Lam, both of Boronia, Australia; David Alexander Tainsh; Trevor Leslie Ilott, both of Ware, United Kingdom

[73] Assignee: Glaxo Wellcome Australia Ltd., Victoria, Austria

[21] Appl. No.: 08/737,592

[22] PCT Filed: May 19, 1995

[86] PCT No.: PCT/EP95/01913

§ 371 Date: Feb. 7, 1997

§ 102(e) Date: Feb. 7, 1997

[87] PCT Pub. No.: WO95/31964

PCT Pub. Date: Nov. 30, 1995

[30] Foreign Application Priority Data

May 21, 1994 [GB] United Kingdom ............... 9410222

[51] Int. Cl.$^6$ ....................................... A61K 9/12
[52] U.S. Cl. ............................... 424/45; 424/46
[58] Field of Search ........................ 424/45, 46

[56] References Cited

U.S. PATENT DOCUMENTS

| | | | |
|---|---|---|---|
| 5,118,494 | 6/1992 | Schultz et al. | 424/45 |
| 5,225,183 | 7/1993 | Purewal et al. | 424/45 |
| 5,301,664 | 4/1994 | Sievers et al. | 128/200.23 |
| 5,605,674 | 2/1997 | Purewal et al. | 424/45 |
| 5,658,549 | 8/1997 | Akehurst et al. | 424/47 |
| 5,674,860 | 10/1997 | Carling et al. | 514/171 |
| 5,849,265 | 12/1998 | Li-Bovet et al. | 424/45 |

FOREIGN PATENT DOCUMENTS

| | | |
|---|---|---|
| 9311745 | 6/1993 | WIPO . |
| 93/17665 | 9/1993 | WIPO . |

OTHER PUBLICATIONS

Ainge et al., *Drug Investigation*, vol. 8, No. 3, 1994, 127–133.

Scadding et al., *Rhinology*, vol. 11, 1993, 37–43.

*Primary Examiner*—Raj Bawa
*Attorney, Agent, or Firm*—Bacon & Thomas, PLLC

[57] ABSTRACT

Suspension formulations suitable for nebulization, for administration by inhalation, comprising fluticasone propionate with a particle size less than 12 microns, one or more surfactants, one or more buffer agents and water. Also described are a method of preparing such a formulation, a container comprising the formulation, and a method of treating asthma using the formulation.

27 Claims, No Drawings

FLUTICASONE PROPIONATE NEBULIZABLE FORMULATIONS

FIELD OF INVENTION

This invention relates to improvements in or relating to pharmaceutical compositions comprising a fluticasone ester. In particular the invention relates to novel formulations of use in the administration of fluticasone propionate by inhalation.

BACKGROUND OF INVENTION

Fluticasone propionate is the approved name for S-fluoromethyl 6a, 9a-difluoro-11b-hydroxy-16a-methyl-17a-propionyloxy-3-oxandrosta-1, 4-diene 17b carbothioate, a corticosteroid known to exhibit topical anti-inflammatory activity and described and claimed in GB 2088877. In the treatment of asthmatic conditions it has been found to be effective to administer fluticasone propionate in the form of dry powders or aerosols containing small particles of the medicament, conventionally prepared by micronisation. Conventionally, fluticasone propionate aerosols have been administered by means of metered dose inhalers, which are designed to deliver a fixed unit dosage of medicament per actuation or "puff". However, some patients, in particular children and the elderly, have difficulty in coordinating actuation of a metered dose inhaler with inhalation, and are therefore unable to use this mode of administration effectively. Furthermore, a proportion of patients find inhalation of dry powders difficult or unpleasant. There is therefore a demand for a pharmaceutical formulation containing fluticasone propionate in a form suitable for nebulisation.

SUMMARY OF INVENTION

The present invention accordingly provides, in a first aspect, a formulation suitable for nebulisation comprising:
  (a) Fluticasone propionate, substantially all having a particle size of less than 12 microns;
  (b) one or more surfactants;
  (c) one or more buffer agents; and
  (d) water.

Fluticasone propionate may be prepared by methods known in the art, for example, as disclosed in GB 2088877. It will be appreciated that solvates of fluticasone propionate can be prepared and, accordingly, the present invention extends to formulations comprising physiologically acceptable solvates of fluticasone propionate. The particle size of the crystalline material may be reduced by conventional methods, for example, by micronisation, and should be such as to permit inhalation of substantially all the medicament into the lungs upon administration of the nebulised formulation. Suitably the particle size will be in the range of 0.5 to 12 microns, such as 1 to 6 microns.

For introduction of the fluticasone propionate into the lungs, the droplet size of the nebulised formulation is an important parameter. Droplet size depends to some extent on the type of nebuliser used, whether a facemask or a mouthpiece is used and the pressure or flow rate of the compressed gas, as well as on the physical properties of the formulation for nebulisation. The nebulised formulation will be heterodisperse, i.e. droplets will cover a range of sizes. Typically, mean droplet size will be in the range of 0.5 to 15 microns, preferably 0.5 to 10 microns, more preferably less than 5 microns.

The formulation according to the invention desirably contains 0.5 to 10% w/w, preferably 1 to 9% w/w especially 1.5 to 6.5% w/w, of fluticasone propionate relative to the total weight of the solid ingredients of the formulation.

The surfactants used in the formulations of the present invention must be physiologically acceptable upon administration by inhalation. Within this category are included surfactants such as sorbitan trioleate (Span$^R$85), sorbitan mono-oleate, sorbitan monolaurate, polyoxyethylene (20) sorbitan monolaurate, polyoxyethylene (20) sorbitan mono-oleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, glyceryl mono-oleate, polyethylene glycol 400 and glyceryl monolaurate.

Particularly preferred surfactants of use in the formulations of the present invention are sorbitan monolaurate and polyoxyethylene (20) sorbitan monolaurate (also known as polysorbate 20).

Suitably the formulations according to the invention contain 0.25 to 0.75% w/w, preferably 0.4 to 0.6% w/w, especially 0.45 to 0.55% w/w, of surfactant relative to the total weight of the solid ingredients of the formulation.

Preferably, the formulation according to the invention contains sorbitan monolaurate and polyoxyethylene (20) sorbitan monolaurate in a ratio of 1:7.5 to 1:8.25, such as 1:7.7 to 1:8.1.

The formulations according to the invention are buffeted to a pH of from about 5 to about 7, preferably about 6. Suitable buffers are those which are physiologically acceptable upon administration by inhalation. Such buffers include citric acid buffers and phosphate buffers, of which phosphate buffers are preferred. Particularly preferred buffers for use in the formulations of the invention are monosodium phosphate dihydrate and dibasic sodium phosphate anhydrous.

The formulations according to the invention will desirably be isotonic. The formulations may be adjusted to isotonicity by addition of a suitable salt, for example, sodium chloride.

DESCRIPTION OF PREFERRED EMBODIMENTS

Thus, in a preferred embodiment, the formulations according to the invention additionally comprise sufficient sodium chloride, or another suitable pharmaceutically acceptable salt, to provide an isotonic composition.

In a particularly preferred embodiment, the invention provides a formulation suitable for administration by nebulisation, which formulation consists of:
  (a) 0.5–2.2 mg fluticasone propionate (micronised);
  (b) 0.12–0.18 mg polyoxyethylene (20) sorbitan monolaurate;
  (c) 0.015–0.025 mg sorbitan monolaurate;
  (d) 18.5–19 mg monosodium phosphate dihydrate;
  (e) 3.2–3.7 mg dibasic sodium phosphate anhydrous;
  (f) 9.4–9.8 mg sodium chloride; and
  (g) water for injection to 2.0 ml.

Thus, it will be appreciataed that formulations according to the preferred embodiment consist of:
  (a) 0.25–1.1 mgml$^{-1}$ fluticasone propionate (micronised);
  (b) 0.06–0.09 mgml$^{-1}$ polyoxyethylene (20) sorbitan monolaurate;
  (c) 0.0075–0.0125 mgml$^{-1}$ sorbitan monolaurate;
  (d) 9.25–9.5 mgml$^{-1}$ monosodium phosphate dihydrate;
  (e) 1.6–1.85 mgml$^{-1}$ dibasic sodium phosphate anhydrous;

(f) 4.7–4.9 mgml$^{-1}$ sodium chloride; and (g) water.

The formulations according to the invention form weakly flocculated suspensions on standing but, surprisingly, these suspensions have been found to be easily redispersed by mild agitation to provide suspensions with excellent delivery characteristics suitable for use in conventional nebulisers, even after prolonged storage.

The chemical and physical stability and the pharmaceutical acceptability of the formulations according to the invention may be determined by techniques well known to those skilled in the art. Thus, for example, the chemical stability of the components may be determined by HPLC assay, for example, after prolonged storage of the product.

The particle size distribution of the formulations according to the invention on nebulisation may be measured by conventional techniques, for example by cascade impaction or by the "Twin Impinger" analytical process. As used herein reference to the "Twin Impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the formulations to be calculated. As used herein reference to "respirable fraction" means the amount of active ingredient collected in the lower impingement chamber per actuation expressed as a percentage of the total amount of active ingredient delivered per actuation using the twin impinger method described above. The formulations according to the invention have been found to have a respirable fraction of 10% or more by weight of the medicament, such as 10% to 50%, for example 15% to 35%.

The formulations according to the invention may be prepared by conventional methods for the preparation of suspension formulations. Typically the fluticasone propionate is contacted with a small amount of surfactant solution so as to "wet" it before addition to the bulk liquid containing the remaining excipients. Constant mixing is essential to maintain a homogeneous suspension. The bulk suspension is sterilised, conveniently by means of thermal sterilisation using steam. Aliquots of the suspension are conveniently filled into sterile containers, for example unit dose containers such as vials or ampoules which are suitably moulded from thermoplastics.

A further aspect of the present invention comprises a method of treating respiratory disorders such as, for example, asthma, which comprises administration by inhalation of an effective amount of a formulation as herein described.

Formulations of the present invention can, thus, be delivered by a nebuliser in which case aliquots of the suspension formulation are desirably filled into sterile containers as described above. Alternatively, the formulations of the present invention can be used as a nasal drop presentation. Thus, aliquots of the suspension formulation are desirably filled into sterile, small volume containers adapted for that delivery route.

The invention is further illustrated by the following non-limiting examples.

| Example 1 | mg |
|---|---|
| Fluticasone propionate (micronised) | 0.525 |
| Polyoxyethylene (20) sorbitan monolaurate | 0.14 |
| Sorbitan monolaurate | 0.018 |
| Monosodium phosphate dihydrate | 18.80 |

-continued

| Example 1 | mg |
|---|---|
| Dibasic sodium phosphate anhydrous | 3.50 |
| Sodium chloride | 9.60 |
| Water for injection | to 2.00 ml |

It will be appreciated that the formulation prepared according to Example 1 consists of:

about 0.26 $mgml^{-1}$ fluticasone propionate (micronised);

about 0.07 $mgml^{-1}$ polyoxyethylene (20) sorbitan monolaurate;

about 0.009 $mgml^{-1}$ sorbitan monolaurate;

about 9.4 $mgml^{-1}$ monosodium phosphate dihydrate;

about 1.75 $mgml^{-1}$ dibasic sodium phosphate anhydrous;

about 4.8 $mgml^{-1}$ sodium chloride; and water.

The formulation prepared according to Example 1 was filled into a nebuliser. The particle size distribution on nebulisation was measured as percentage of fluticasone propionate in Stage 2 (fine particle fraction) of the Twin Impinger apparatus and as percentage of fluticasone propionate in Stages 2–7 (fine particle fraction) of the cascade impactor apparatus. Values of 18.5% and 18.2% respectively were obtained.

| Example 2 | mg |
|---|---|
| Fluticasone propionate (micronised) | 2.10 |
| Polyoxyethylene (20) sorbitan monolaurate | 0.16 |
| Sorbitan monolaurate | 0.02 |
| Monosodium phosphate dihydrate | 18.80 |
| Dibasic sodium phosphate anhydrous | 3.50 |
| Sodium chioride | 9.60 |
| Water for injection | to 2.00 ml |

It will be appreciated that the formulation prepared according to Example 2 consists of:

about 1.05 $mgml^{-1}$ fluticasone propionate (micronised);

about 0.08 $mgml^{-1}$ polyoxyethylene (20) sorbitan monolaurate;

about 0.01 $mgml^{-1}$ sorbitan monolaurate;

about 9.4 $mgml^{-1}$ monosodium phosphate dihydrate;

about 1.75 $mgml^{-1}$ dibasic sodium phosphate anhydrous;

about 4.8 $mgml^{-1}$ sodium chloride; and water.

The formulation prepared according to Example 2 was filled into a nebuliser. The particle size distribution on nebulisation was measured as for Example 1. Values of 22.1% for the Twin Impinger apparatus test and 21.6% for the cascade impactor apparatus test were obtained.

We claim:

1. A suspension formulation suitable for nebulization, for delivering to the lungs an effective amount of the formulation, said formulation comprising:

(a) fluticasone propionate having a particle size of less than 12 microns;

(b) one or more surfactants;

(c) one or more buffer agents; and (d) water.

2. A suspension formulation suitable for nebulization, for delivering to the lungs an effective amount of the formulation, said formulation consisting essentially of:

(a) fluticasone propionate having a particle size of less than 12 microns;

(b) one or more surfactants;

(c) one or more buffer agents; and (d) water.

3. A formulation according to claim 1, wherein the fluticasone propionate has a particle size of 1 to 6 microns.

4. A formulation according to claim 2, wherein the fluticasone propionate has a particle size of 1 to 6 microns.

5. A formulation according to claim 1, wherein the fluticasone propionate is present in an amount of 0.5 to 10% w/w based on the total weight of the solid ingredients of the formulation.

6. A formulation according to claim 2, wherein the fluticasone propionate is present in an amount of 0.5 to 10% w/w based on the total weight of the solid ingredients of the formulation.

7. A formulation according to claim 2, wherein the formulation contains two surfactants.

8. A formulation according to claim 1, wherein the surfactant is present in an amount of 0.25% to 0.75% w/w of the total weight of the solid ingredients of the formulation.

9. A formulation according to claim 2, wherein the surfactant is present in an amount of 0.25% to 0.75% w/w of the total weight of the solid ingredients of the formulation.

10. A formulation according to claim 1, wherein the surfactants are selected from the group consisting of sorbitan trioleate, sorbitan mono-oleate, sorbitan monolaurate, polyoxyethylene (20) sorbitan monolaurate, polyoxyethylene (20) sorbitan mono-oleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, glyceryl mono-oleate, polyethylene glycol 400 and glyceryl monolaurate.

11. A formulation according to claim 2, wherein the surfactants are selected from the group consisting of sorbitan trioleate, sorbitan mono-oleate, sorbitan monolaurate, polyoxyethylene (20) sorbitan monolaurate, polyoxyethylene (20) sorbitan mono-oleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, glyceryl mono-oleate, polyethylene glycol 400 and glyceryl monolaurate.

12. A formulation according to claim 10, wherein the surfactants are sorbitan monolaurate and polyoxyethylene (20) sorbitan monolaurate.

13. A formulation according to claim 11, wherein the surfactants are sorbitan monolaurate and polyoxyethylene (20) sorbitan monolaurate.

14. A formulation according to claim 12, wherein the sorbitan monolaurate and polyoxyethylene (20) sorbitan monolaurate are present in a ratio of 1:7.5 to 1:8.25.

15. A formulation according to claim 13, wherein the sorbitan monolaurate and polyoxyethylene (20) sorbitan monolaurate are present in a ratio of 1:7.5 to 1:8.25.

16. A formulation according to claim 1 which is buffered to a pH of from about 5 to about 7.

17. A formulation according to claim 2 which is buffered to a pH of from about 5 to about 7.

18. A formulation according to claim 1 which is isotonic.

19. A formulation according to claim 2 which is isotonic.

20. A formulation according to claim 1 comprising:

(a) 0.25–1.1 $mgml^{-1}$ fluticasone propionate (micronised);

(b) 0.06–0.09 $mgml^{-1}$ polyoxyethylene (2) sorbitan monolaurate;

(c) 0.0075–0.0125 $mgml^{-1}$ sorbitan monolaurate;

(d) 9.25–9.5 $mgml^{-1}$ monosodium phosphate dihydrate;

(e) 1.6–1.85 $mgml^{-1}$ dibasic sodium phosphate anhydrous;

(f) 4.7–4.9 $mgml^{-1}$ sodium chloride; and (g) water.

21. A formulation according to claim 20 comprising:

(a) about 0.26 $mgml^{-1}$ fluticasone propionate (micronised);

(b) about 0.07 $mgml^{-1}$ polyoxyethylene (20) sorbitan monolaurate;

(c) about 0.009 $mgml^{-1}$ sorbitan monolaurate;

(d) about 9.4 $mgml^{-1}$ monosodium phosphate dihydrate;

(e) about 1.75 $mgml^{-1}$ dibasic sodium phosphate anhydrous;

(f) about 4.8 $mgml^{-1}$ sodium chloride; and (g) water.

22. A formulation according to claim 20 comprising:

(a) about 1.05 $mgml^{-1}$ fluticasone propionate (micronised);

(b) about 0.08 $mgml^{-1}$ polyoxyethylene (20) sorbitan monolaurate;

(c) about 0.01 $mgml^{-1}$ sorbitan monolaurate;

(d) about 9.4 $mgml^{-1}$ monosodium phosphate dihydrate;

(e) about 1.75 $mgml^{-1}$ dibasic sodium phosphate anhydrous;

(f) about 4.8 $mgml^{-1}$ sodium chloride; and (g) water.

23. A method of preparing a formulation according to claim 1 comprising contacting the fluticasone propionate with a solution of surfactant and mixing the resultant drug/surfactant solution with the other components of the formulation.

24. A container comprising a formulation according to claim 1.

25. A method of treating asthma which comprises administration by inhalation via a nebulizer of an effective amount of a formulation as claimed in claim 1.

26. A method according to claim 25 in which the nebulizer produces a plurality of droplets of the formulation prior to inhalation.

27. A suspension formulation suitable for nebulization, for delivering to the lungs an effective amount of the formulation, said formulation comprising:

(a) fluticasone propionate having a particle size of less than 12 microns;

(b) two surfactants;

(c) one or more buffer agents; and (d) water.

* * * * *